(12) United States Patent
Murphy

(10) Patent No.: US 8,834,481 B2
(45) Date of Patent: *Sep. 16, 2014

(54) CEMENT DELIVERY NEEDLE

(76) Inventor: Kieran Murphy, Baltimore, MD (US)

( * ) Notice: Subject to any disclaimer, the term of this patent is extended or adjusted under 35 U.S.C. 154(b) by 1481 days.

This patent is subject to a terminal disclaimer.

(21) Appl. No.: 11/661,838

(22) PCT Filed: Sep. 6, 2005

(86) PCT No.: PCT/US2005/031605
§ 371 (c)(1),
(2), (4) Date: Dec. 13, 2007

(87) PCT Pub. No.: WO2006/031490
PCT Pub. Date: Mar. 23, 2006

(65) Prior Publication Data
US 2008/0200916 A1 Aug. 21, 2008

Related U.S. Application Data

(60) Provisional application No. 60/608,620, filed on Sep. 10, 2004.

(51) Int. Cl.
| | |
|---|---|
| A61B 17/56 | (2006.01) |
| A61B 17/88 | (2006.01) |
| A61B 19/02 | (2006.01) |
| A61F 2/46 | (2006.01) |
| A61B 17/00 | (2006.01) |

(52) U.S. Cl.
CPC ......... *A61B 17/8822* (2013.01); *A61B 19/0271* (2013.01); *A61F 2002/4635* (2013.01); *A61B 17/00234* (2013.01)
USPC ............................................. 606/94; 606/93

(58) Field of Classification Search
USPC ...................................................... 606/92–94
See application file for complete search history.

(56) References Cited

U.S. PATENT DOCUMENTS

| | | | | |
|---|---|---|---|---|
| 6,033,411 A | * | 3/2000 | Preissman ........................ | 606/99 |
| 6,149,655 A | * | 11/2000 | Constantz et al. .............. | 606/94 |
| 6,241,734 B1 | * | 6/2001 | Scribner et al. ................. | 606/93 |
| 6,348,055 B1 | * | 2/2002 | Preissman ........................ | 606/94 |
| 6,602,229 B2 | * | 8/2003 | Coss ............................. | 604/187 |
| 6,620,169 B1 | * | 9/2003 | Peterson et al. ................ | 606/93 |
| 7,488,329 B2 | * | 2/2009 | Thelen et al. .................. | 606/99 |
| 2003/0018292 A1 | * | 1/2003 | Kuslich et al. ................. | 604/11 |

FOREIGN PATENT DOCUMENTS

| | | |
|---|---|---|
| EP | 1 212 993 A2 | 6/2002 |
| WO | WO 03/094805 A2 | 4/2003 |
| WO | WO 2005/025450 A2 | 3/2005 |

OTHER PUBLICATIONS

International Search Report dated Jan. 13, 2006 for International Application No. PCT/US2005/031605.

*Primary Examiner* — Christopher Beccia
(74) *Attorney, Agent, or Firm* — Perry + Currier Inc.; Kristjan Spence

(57) ABSTRACT

A cement delivery needle apparatus (20) and a method of flowing a bone cement through a vertebroplasty needle apparatus are provided. The cement delivery needle apparatus (20) includes a sheath (24) and a handle (26). The sheath (24) has an inlet (44) to receive a bone cement and an outlet (40) for expressing the cement into a vertebral body. The handle (26) extends from the sheath (24) and includes a vibration assembly (70) for agitating the cement. The method includes providing a bone cement source to the needle. The method further includes providing a vibration assembly associated with a handle of the needle, agitating the cement with the vibration assembly and injecting the cement through the sheath.

31 Claims, 16 Drawing Sheets

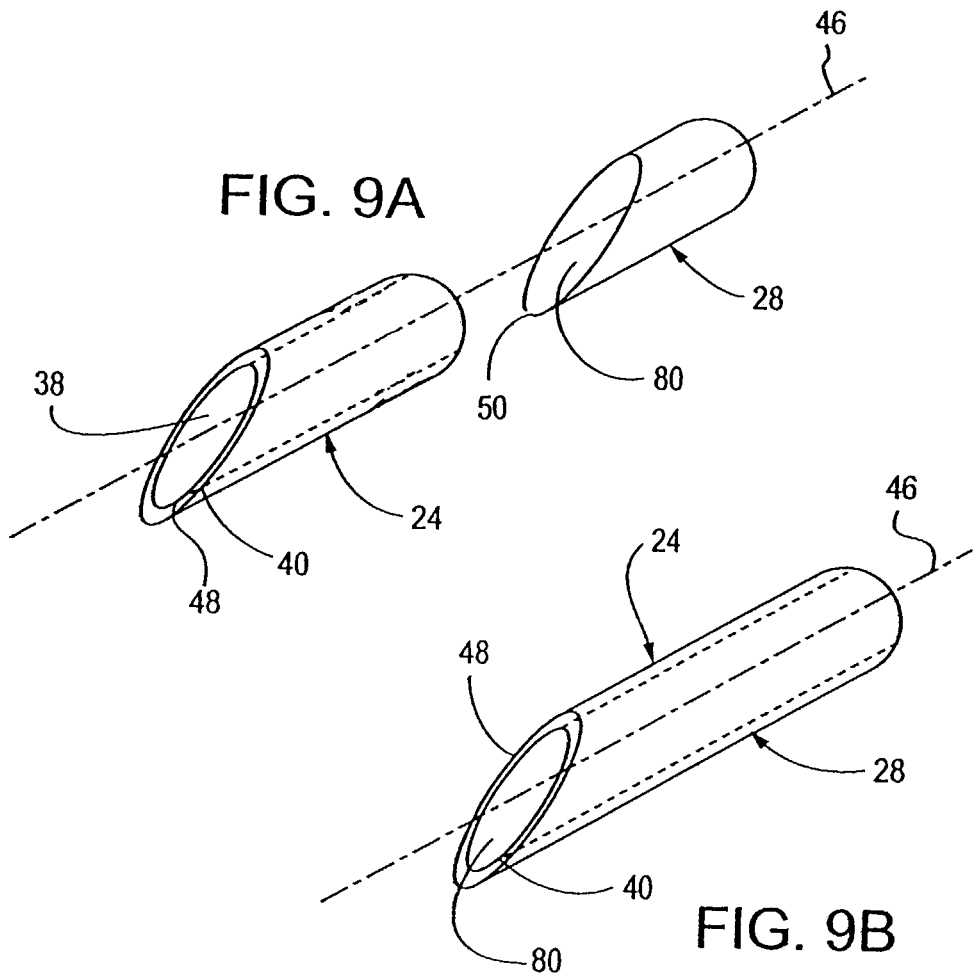
FIG. 9A
FIG. 9B
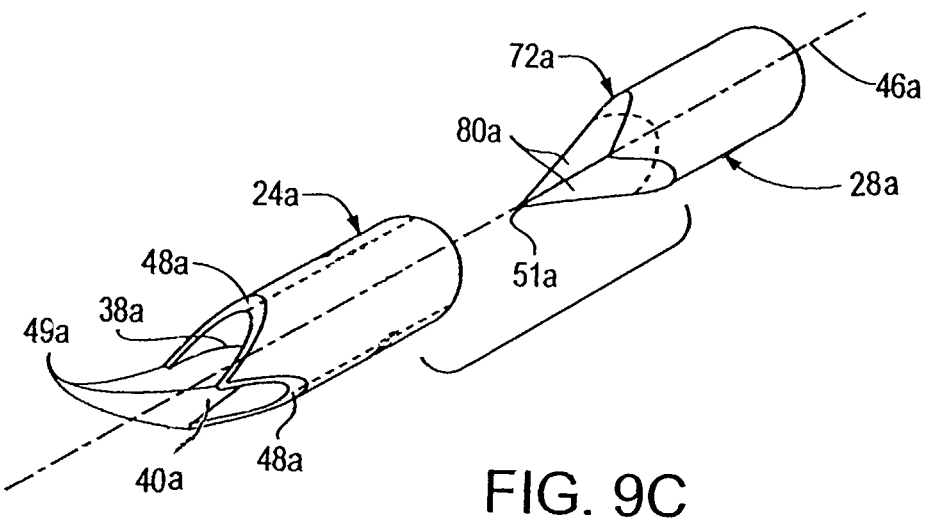
FIG. 9C

CEMENT DELIVERY NEEDLE

This application is a continuation of International Application No. PCT/US2005/031605, filed Sep. 6, 2005, which is claims the benefit of U.S. Provisional Application Ser. No. 60/608,620, filed Sep. 10, 2004, these references are incorporated herein in their entirety.

FIELD OF THE INVENTION

This application relates to an apparatus and system for performing vertebroplasty. In particular, this application relates to a surgical needle for expressing bone cement into a vertebral body.

BACKGROUND OF THE INVENTION

Percutaneous vertebroplasty involves the injection of a bone cement or suitable biomaterial into a vertebral body via a percutaneous route under X-ray, ultrasonic, magnetic resonance imaging, or other visual guidance. The cement is injected as a semi-liquid substance through a needle that has been inserted into the vertebral body, generally along a transpedicular or posterolateral approach. The three main indications for vertebroplasty are benign osteoporotic fractures, malignant metastatic disease and benign tumors of the bone. Traumatic fractures of weakened bone or traumatic fractures of normal bone can also be treated by the methods described here. The bone cement materials injected into a vertebral body may be derivatives of polymethyl methacrylate (PMMA) or biologically active substances such as calcium triphosphate, calcium phosphate or hydroxyapetite or bone morphogenic protein (BMP).

Percutaneous vertebroplasty provides structural reinforcement of a vertebral body through injection, by a minimally invasive percutaneous approach, of bone cement material into the vertebral body. See, for example, Vasconcelos, C. et al., Is percutaneous vertebroplasty without pretreatment venography safe? Evaluation of 205 consecutive procedures. *Am. J. Neuroradiol.* 2002, June-July; 23(6): 913-7. Percutaneous vertebroplasty can result in increased structural integrity, decreased micromotion at the fracture site, and possibly a destruction of pain fibers due to the heat of the bone cement as it polymerizes and sets. Complete pain relief can be achieved in up to eighty percent of patients. The cement material should have properties that, when injected, can increase vertebral body stiffness and compressive strength. Any cement materials having these properties that are commonly known or become known to one of skill in the art may be used. The cement should be fluid enough to flow into fracture planes and to fuse them. Although there is some debate about the appropriate thermal properties, it is believed by some that the heating effect can be beneficial and cause death to local nerve endings involved in pain stimulation. It is generally accepted that most pain relief is achieved due to increased structural integrity.

When performing vertebroplasty, a needle of an appropriate gauge (for example, an eleven gauge or thirteen gauge in a smaller vertebral body) is passed down the pedicle until it enters the vertebral body and reaches the junction of the anterior and middle thirds. The needle is inserted at a suitable angle and passed through the periosteum, down the pedicle and into the vertebral body. Insertion of the needle may require a large applied force. For example, a large force may be required when entering the cortex and in the transition from the pedicle to the vertebral body.

A suitable cement material is prepared, injected through the needle and into the vertebral body, under lateral X-ray projection fluoroscopy imaging. Injection of the cement continues until adequate vertebral filling is achieved. The injection is discontinued if the cement starts to extend into some unwanted location such as the disc space or towards the posterior quarter of the vertebral body, where the risk of epidural venous filling and hence spinal cord compression is greatest.

Exemplary needles for use in vertebroplasty are disclosed in U.S. Pat. No. 6,749,595, which is incorporated herein by reference. Typically, an injector system or a syringe may be attached to the needle for pressurized delivery of the cement to the vertebral body. Due to the high pressure used to inject the cement into the vertebral body, complications of vertebroplasty include a risk of extravasation of cement into the venous system and further embolization to the lungs. These complications can cause cord compression and paralysis or pulmonary embolism and death. Murphy et al., A Review of Complications Associated with Vertebroplasty and Kyphoplasty as Reported to the Food and Drug Administration Medical Device Related Web Site, *Journal of Vascular and Interventional Radiology*, in press.

Thus, a need exists for a cement delivery apparatus that can withstand the rigors of insertion into a patient undergoing percutaneous vertebroplasty and that allows for delivery cement in a controlled manner to avoid complications associated with high pressure delivery of the cement to the vertebral body.

BRIEF SUMMARY OF THE INVENTION

This application provides a cement delivery needle apparatus that may be used to perform percutaneous vertebroplasty. The cement delivery needle apparatus may include a sheath and a handle. The sheath may have an inlet to receive a bone cement and an outlet for expressing the cement into a vertebral body. The handle extends from the sheath and may include a vibration assembly for agitating the cement.

A method of flowing a bone cement through a vertebroplasty needle apparatus is also provided. The method includes providing a bone cement source to the apparatus, providing a vibration assembly associated with a handle of the needle, agitating the cement with the vibration assembly and injecting the cement through the sheath.

A kit for use in performing vertebroplasty is also provided. The kit may include a local anesthesia assembly, a surgical cutting instrument, a cement assembly for injection into a vertebral body, and a cement delivery needle apparatus as described here. The cement delivery needle apparatus includes a sheath and a handle extending from the sheath, where the sheath has an inlet to receive a bone cement and an outlet for expressing the cement into a vertebral body, and the handle includes a vibration assembly for agitating the cement.

A cement delivery system is also provided. The cement delivery system includes a cement delivery needle, a sheath having an inlet to receive a bone cement and an outlet for expressing the cement into a vertebral body, a handle extending from the sheath, an injector having a barrel operably connected to the needle; and a vibration assembly disposed against the barrel for agitating the cement. Alternatively or in addition to an injector, the system may include a connector operably connected to the needle; and a vibration assembly disposed against the connector for agitating the cement Advantages of the present invention will become more apparent to those skilled in the art from the following description of the preferred examples of the present invention that have been shown and described by way of illustration. As will be realized, the invention is capable of other and different examples, and its details are capable of modification in various respects. Accordingly, the drawings and description are to be regarded as illustrative in nature and not as restrictive.

BRIEF DESCRIPTION OF SEVERAL VIEWS OF THE DRAWINGS

The cement delivery needle apparatus will be described in further detail with reference to the figures.

FIG. 9A is an exploded partial perspective view of the needle apparatus of FIG. 1;

FIG. 9B is a partial perspective view of the needle apparatus of FIG. 1;

FIG. 9C is a partial perspective view of an alternative tip of the needle apparatus of FIG. 1;

DETAILED DESCRIPTION OF THE INVENTION

Figure 1:
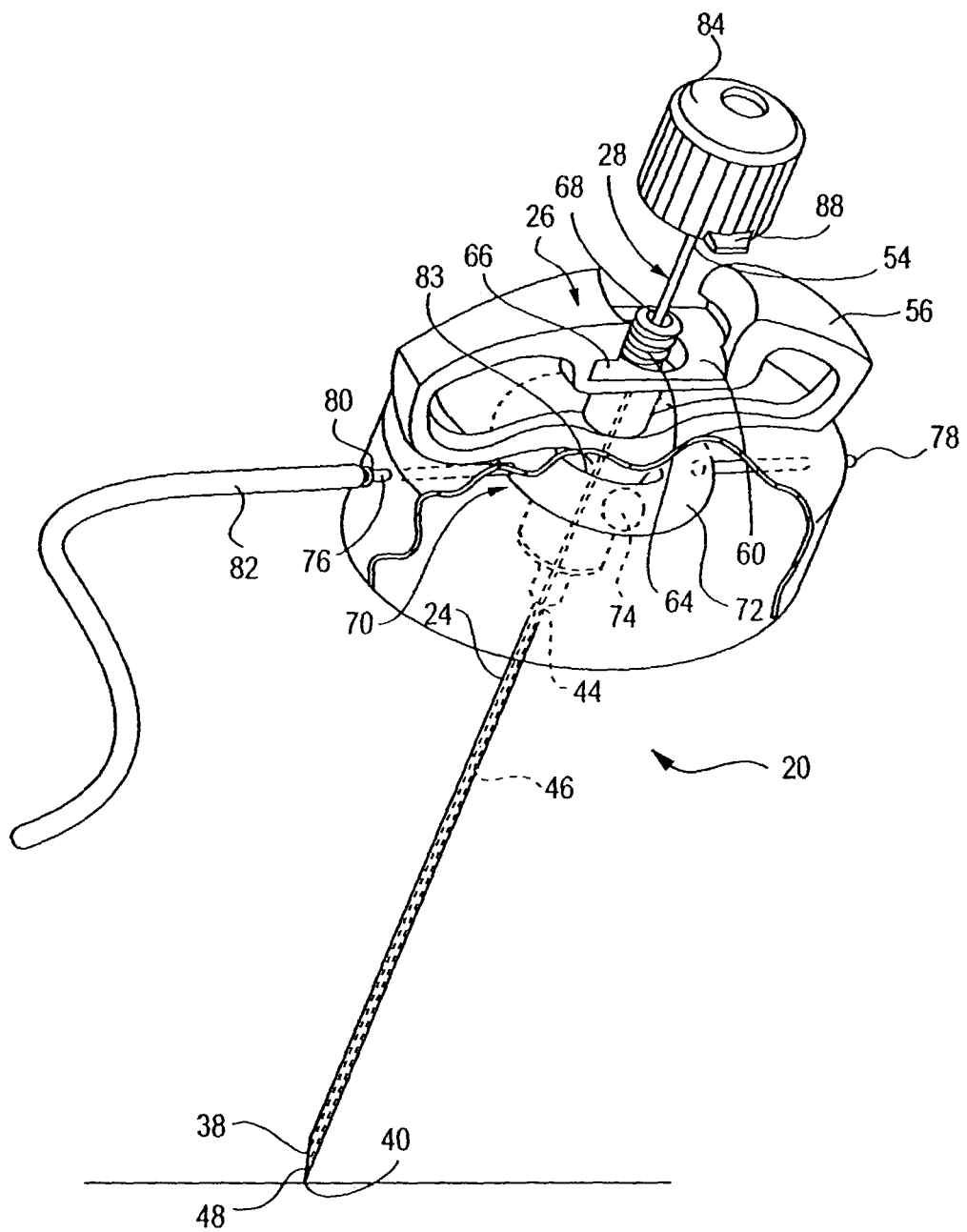
FIG. 1 is a perspective view of a cement delivery needle apparatus.

A cement delivery needle apparatus 20 is shown in FIG. 1. The needle apparatus 20 may be used for expressing a bone cement into a target site, for example, a vertebral body. By way of example, bone cement materials include, but are not limited to, polymethyl methacrylate (PMMA) and biologically active substances such as calcium triphosphate, calcium phosphate, hydroxyapetite or bone morphogenic protein (BMP). Portions of the needle apparatus 20 may be constructed of surgical grade stainless steel, but other suitable materials known to one of skill in the art, that are also compatible with magnetic resonance imaging may be used.

The cement delivery needle apparatus 20 shown in the example of FIG. 1 includes a sheath 24, a handle 26 and an insert 28 receivably removable within the sheath 24. The insert 28 is receivable within the sheath 24 for insertion of the needle apparatus 20 into a vertebral body 32 via a percutaneous route. The insert 28 is removable from the sheath 24 to facilitate the injection of a cement 36 into a vertebral body 32.

The sheath 24 may be a generally a hollow cylinder with an interior 38, an outlet 40 and an inlet 44. The sheath 24 may be cylindrically centered about an axis 46 and, as shown in the example in FIG. 1, the cross-sectional area of interior 38 may not be reduced at the outlet 40. As shown, the outlet 40 may be beveled such that the outlet 40 presents a single planar face 48. The planar face 48 may be at an angle from about 15° to about 75° to axis 46, for example, about 30° to about 60°. However, the planar face 48 may be at any angle.

As shown in FIGS. 9A and 9B, the insert 28 may be generally cylindrical with a tip 50. The tip 50 may be beveled at substantially the same angle as the outlet 40 of the sheath 24 creating a beveled face 80. When the insert 28 is received within the sheath 24, the insert 28 may be oriented such that the tip 50 is flush with the outlet 40. As shown in FIG. 9B, the planar face 48 may be aligned with the beveled face 80.

FIG. 9C illustrates an alternative insert 24a and sheath 28a similar to the insert 24 and sheath 28 described above and given the same numeral with the suffix a. The sheath 24a is cylindrically centered about axis 46a and may include three substantially equal, inwardly beveled surfaces 48a defining an outlet 40a. The sheath 24a may include three sharp points 49a at outlet 40a. Each sharp point 49a may be present at each intersection of two beveled surfaces 48a. Each beveled surface 48a is at about the same angle to axis 46a. Each planar face 46a may be about 15° to about 75° to axis 46a, for example, about 30° to about 60° and about 45°. However, the planar face 48a may be at any angle.

The insert 28a is generally cylindrical with a tip 72a. The tip 72a has three substantially equal, inwardly beveled faces 80a. Each face 80a is beveled at substantially the same angle as beveled surfaces 48a. Thus, all three beveled faces 80a intersect at a leading point 51a that protrudes from the sheath 24a. When the insert 28a is received within sheath 24a, insert 28a can be oriented such that each of the beveled faces 80a is aligned with one of the beveled surfaces 48a. The bevel angle is substantially similar between the insert 28a and the sheath 24a, thus there is no step from the tip 72a to the sheath 24a, to present three continuous beveled faces from sheath 24a to tip 72a. Exemplary needles having the insert 24, 24a and the sheath 28, 28a may be in the Osteo-Sitee bone biopsy needle sets, including the Murphy Side Bevel/Back M1M and Murphy Diamond Bevel M2 available from Cook, Incorporated, Bloomington, Ind. and are described in U.S. Pat. No. 6,749,595.

The inlet 44 of the sheath 24 may be fixed to the handle 26 for grasping by the operator as shown in FIG. 1. The inlet 44 may be fixed to the handle 26 by friction fit or other means known to one of skill in the art. The handle 26 may be a molded polymer, but other material and processes are also contemplated.

Figure 2A:
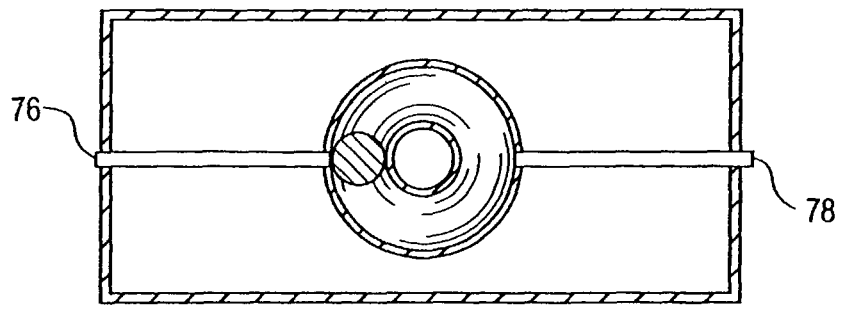
FIG. 2A is a cross-sectional view of a handle of the needle apparatus shown in FIG. 1.
Figure 2B:
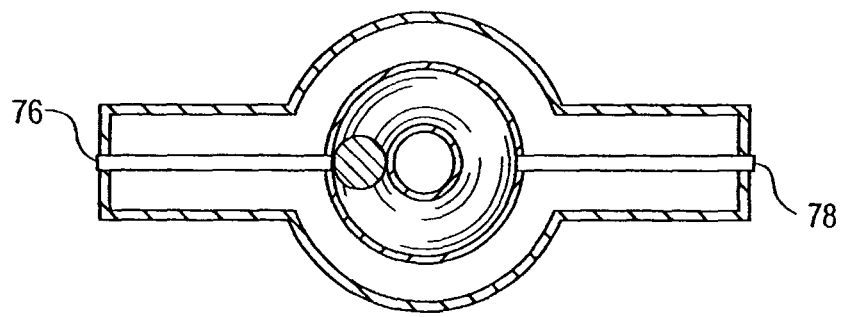
FIG. 2B is cross-sectional view of an alternative handle of the needle apparatus shown in FIG. 1.

The handle 26 may be any shape suitable for grasping by an operator. FIGS. 2A and 2B illustrate cross sectional views of two exemplary shapes for the handle 26. As shown in FIG. 1, for example, the handle 26 may have two wings 56 for grasping. A connector 60 may be formed within the handle 26. The connector 60 may be a female Luer connector. The connector 60 may have an externally threaded center post 64 and internal sleeves 66. The center post 64 may have a hollow interior 68 that is aligned with and extends from the interior 38 of the sheath 24, forming a continuous cylindrical hollow from the handle 26 to the outlet 40.

The handle 26 shown in FIG. 1 further may include a vibration assembly 70 operably connected to the handle 26 for agitating the cement 36 for injection of the cement 36 into the vertebral body 32 through the sheath 24. The vibration assembly 70 may be constructed as part of the handle 26, for example, but not limited to integrally molding the vibration assembly 70 at least partially into the handle 26. Alternatively, the vibration assembly 70 may be removably connected to the handle 26 once the needle apparatus 20 is inserted into the vertebral body 32. (See FIG. 6.) The cement 36 may be agitated prior to injection, during injection or any combinations thereof.

As shown in FIG. 1, the vibration assembly 70 may include a chamber 72 surrounding the center post 64 of the handle 26. The chamber 72 may be formed integral with the handle 26. The chamber 72 may contain vibrational member 74, for example, a dense metallic spherically shaped body, such as a ball bearing. A plurality of vibrational members 74 may be in the chamber 72 as shown in FIG. 3. The vibrational member(s) 74 and the chamber 72 may be radiolucent. Other vibrational members known to one of skill in the art, such as a roller that may be cylindrical, tapered, or spherically shaped, may be used in the chamber 72. The chamber 72 may further include an inlet port 76 and an outlet port 78. Alternatively, a plurality of outlet ports 78 may exit from the chamber 72 (as shown in FIG. 3). The ports 76, 78 may be formed in the handle 26 and connect to the chamber 72. The inlet port may include a Luer connector 80 for attachment of tubing 82 connected to a compressed air source or other energy source (not shown). In operation, compressed air enters the inlet port 76 to cause the vibrational member 74 to vibrate and oscillate within the chamber 72, vibration of the chamber 72 provides vibration to the post 64 and any body attached to the vibration assembly 70. The pressurized air flow is from inlet port 76 to the chamber 72 and out the outlet port 78. Pressurized air may be provided by any source known to one of skill in the art. The pressurized air source may be removably connected via tubing 82 or any other means known to one of skill in the art. The connection of the tubing 82 to the inlet 76 may occur before or after placement of the needle 20 in the vertebral body 32. For example, connection after the placement of the needle 20 may minimize any obscuring of the target site for the needle 20 insertion by any radiodense materials in the needle 20. The handle 26 or tubing 82 may further include a switch 81 for controlling the supply of the air flow. The switch 81 may include on and off positions.

The connector 60 of the handle 26 of the needle 20 may releasably receive a plurality of attachments. As shown in FIG. 1, a complimentary connector 84 may be releasably attached to the connector 60 of the handle 26. The connector 84 may be connected to the insert 28 at an end 54 of the insert 28. The connector 84 also may be internally threaded to receive the externally threaded center post 64 of the connector 60 when the insert 28 is received within the sheath 24. The connector 84 may include external locking arms 88 that are receivable by sleeves 66 when locking the insert 28 within the sheath 24. For example, the connector 60 and the complimentary connector 84 may be Luer locks, however, the connector 60 and the complimentary connector 84 may be any releasable attachment known to one of skill in the art.

Figures 3A, 3B:
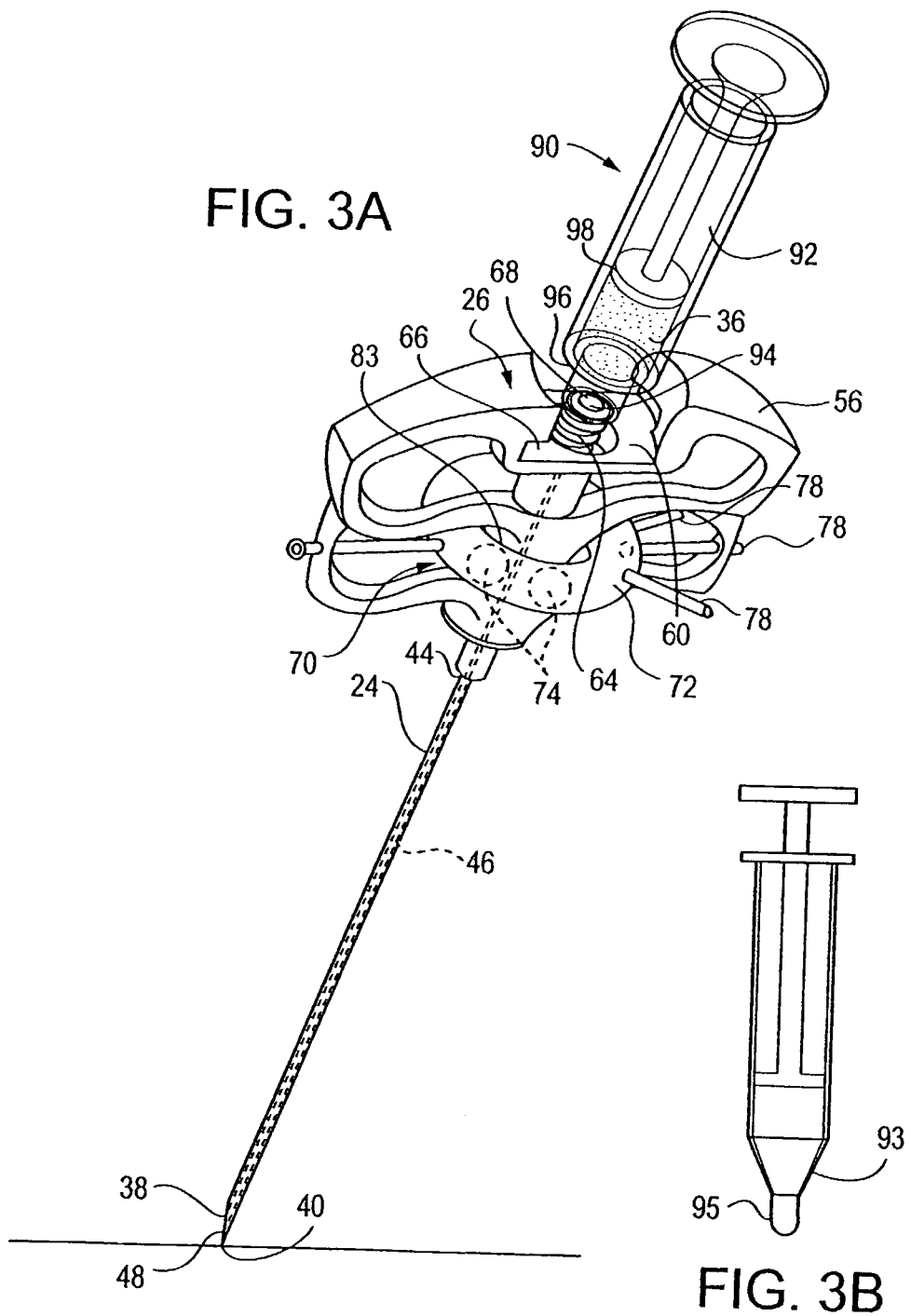
FIG. 3 is a perspective view of a cement delivery needle apparatus showing a syringe attached to the handle of the needle.

An injector 90 may also be releasably attached to the connector 60 of the handle 26 of the needle apparatus 20 as shown in FIG. 3. The injector 90 may be any suitable part for cement delivery through the hollow interior 68 of the handle 26 and the sheath 24 into the vertebral body 32. The injector 90 may include a tapered barrel 93 as shown in FIG. 3B where the barrel 93 tapers to a connector 95, such as a Luer connector, or any connector known to one of skill in the art. For example, the injector 90 may be a syringe 92 containing cement 36 for delivery to the vertebral body 32. Exemplary syringes may be found in the Osteo-Force® High Pressure Injector Set, available from Cook Incorporated, Bloomington, Ind. The Medallion Syringe from Merit Medical Systems Inc., South Jordan, Utah and the DynaTorque Injector from Parallax Medical, Inc., Mountain View, Calif. are also exemplary syringes that may be used.

The syringe 92 may include a complementary connector 94 at an end 96, such as a Luer connector, for releasable attachment of the syringe 92 to the threaded center post 64 of the connector 60. The syringe 92 also may include a plunger 98 for expressing the cement 36 from the syringe 92 into the hollow interior 68 of the center post 64 through the interior 38 of the sheath 24 into the vertebral body 32. Pressure to express the cement 36 from the syringe 92 may be generated by hand or other application of force to the plunger 98.

Figure 4:
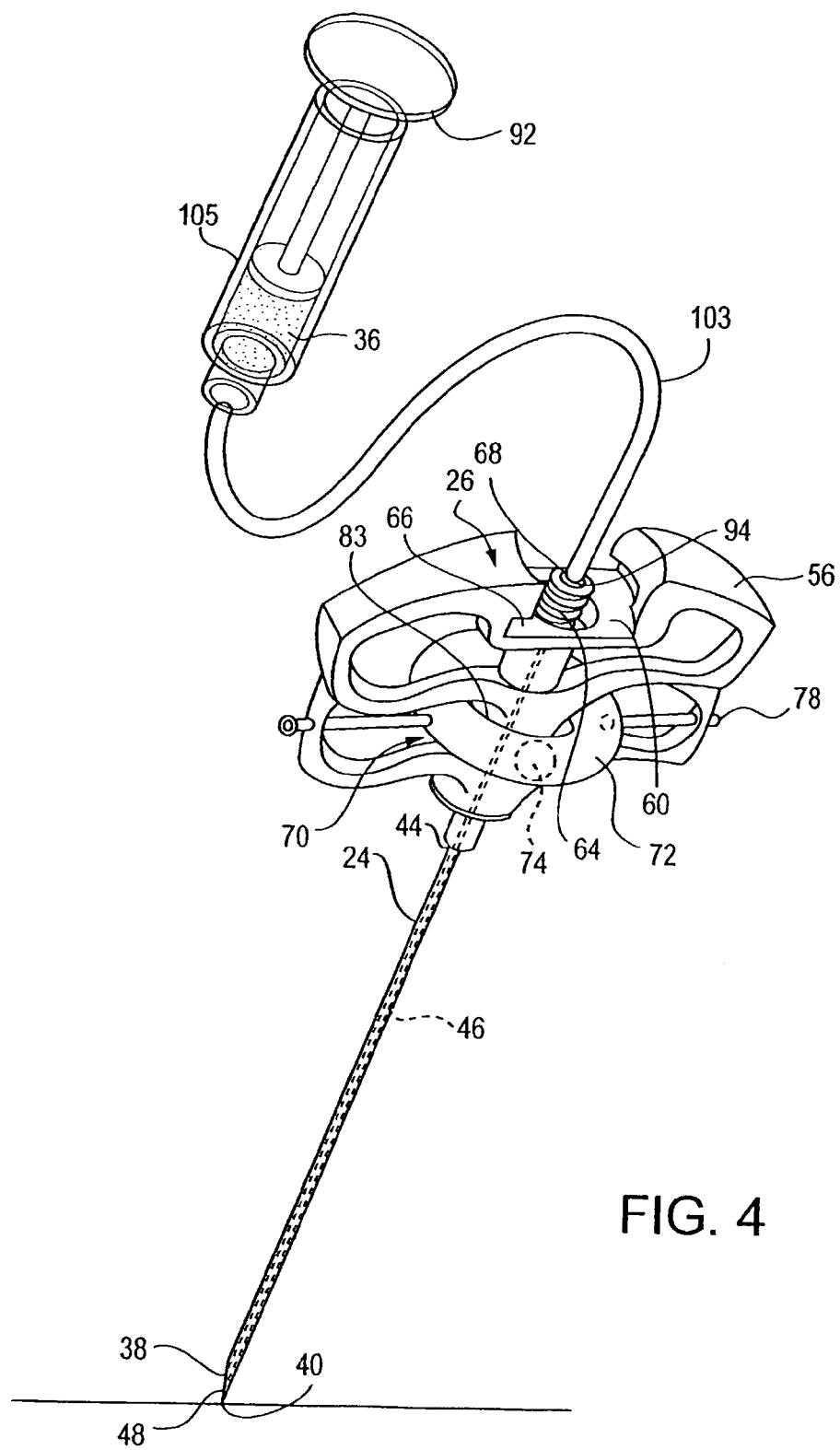
FIG. 4 is a perspective view of a cement delivery needle apparatus showing a connecting tubing attached to the handle of the needle.

As shown in FIG. 4, a connecting tube 103 may be removably attached to the connector 60 of the handle 26. A syringe 105 containing the cement 36 may be removably attached to the connecting tube 103. The attachments between the connecting tube 103, the syringe 105 and the connector 60 may be Luer connectors or any connectors known to one of skill in the art.

Figure 5:
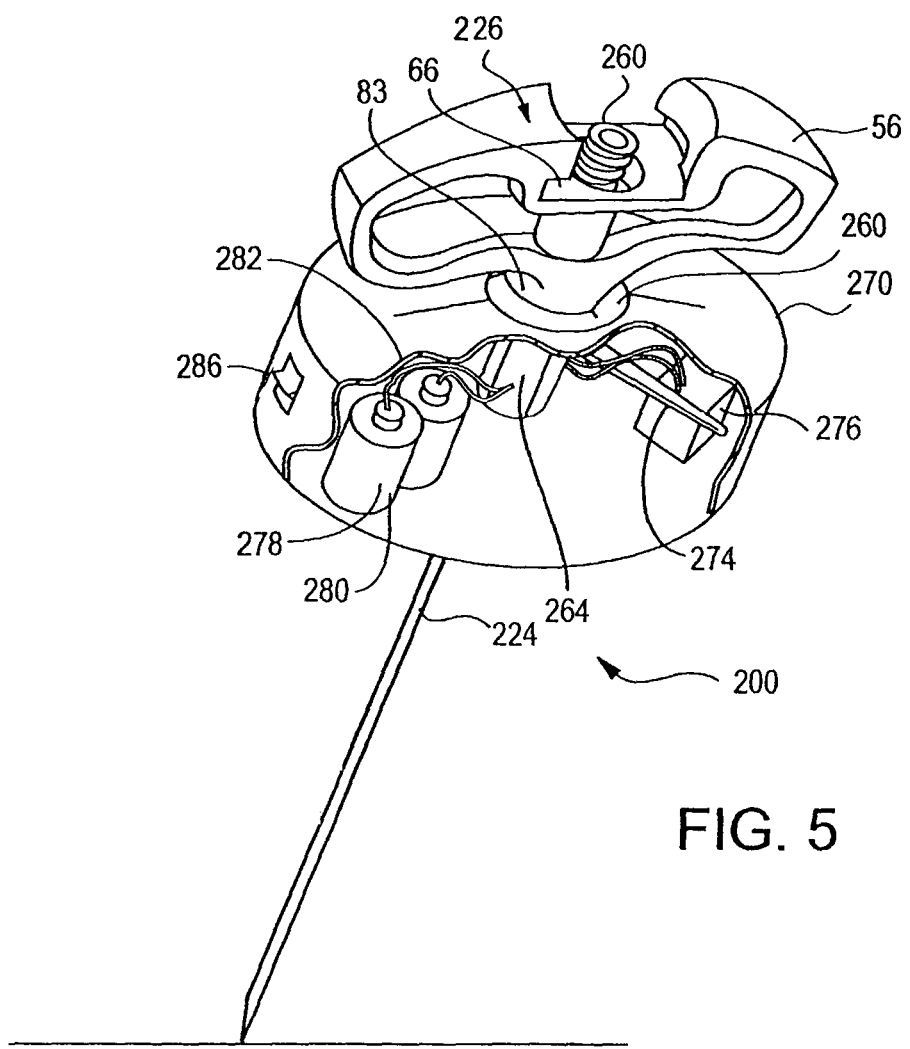
FIG. 5 is a perspective view of another cement delivery needle apparatus.

As shown in FIG. 5, a cement delivery needle apparatus 200, similar to the cement delivery needle apparatus 20, may include a handle 226 having a vibration assembly 270 operably connected to the handle 226 for agitating the cement 36 for injection of the cement 36 into the vertebral body 32 through the sheath 224. The vibration assembly 270 may be constructed as part of the handle 226, for example, but not limited to integrally molding the vibration assembly 270 at least partially into the handle 226. Alternatively, the vibration assembly 270 may be removably connected to the handle 226 once the needle 200 is inserted into the vertebral body 32. The cement 36 may be agitated prior to injection, during injection or any combinations thereof.

The vibration assembly 270 may include an arm 274, which can be mounted in various ways within the handle 226 to provide vibration to the post 264 and any body attached to the vibration assembly 270. The arm 274 may be driven by a motor 276 that is actuated by a driver assembly 278 located in the handle 226. For example, the motor 276 and the driver assembly 278 may be balanced in weight on either side of the handle 226 to assist the operator. As shown in FIG. 5, the driver assembly 278 may include at least one battery 280 and a cable 282 connected to the motor.

Alternatively, power may be provided by an electrical source external to the needle apparatus 200. The motor 276 may be electromagnetic, mechanical and/or electromechanical, or any type of motor known to one of skill in the art. A switch 286 may be provided on the handle 226 to control the movement of the vibration assembly 270. The switch 286 may control on/off movement of the arm 274 or the switch 286 may also control the speed with which the arm 274 provides vibration.

Similar to the handle 26 of the needle 20, the handle 226 of the needle 200 shown in FIG. 5 may include a connector 260 that may releasably receive a plurality of attachments. As described above for the connector 60, the connector 260 may releasably receive attachments by way of example, but not limited to, such as a connector having an insert, a syringe, and connecting tubing.

Figure 6:
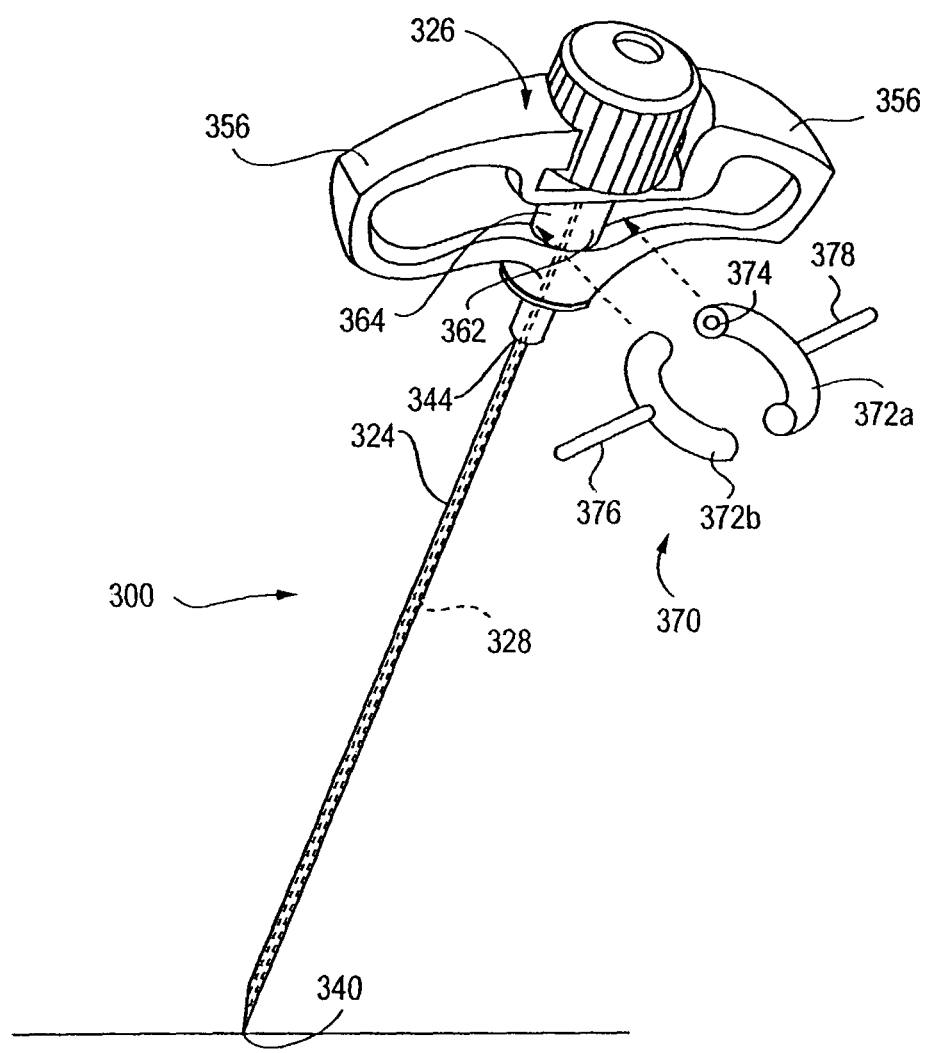
FIG. 6 is a perspective view of yet another cement delivery needle apparatus.

Another cement delivery needle apparatus 300 is shown in FIG. 6. As described above, the vibration assembly may be removably connected to the handle. FIG. 6 illustrates the needle apparatus 300 prior to the attachment of the vibration assembly 370. As shown in this example, the needle apparatus 300 includes a sheath 324, a handle 326 and an insert 328 that is slidably removable from the sheath 324. The handle 326 further includes a vibration assembly attachment site 362 for the attachment of the vibration assembly 370. The vibration assembly 370 may be attached to the site 362 at any time, i.e., prior to use or during use of the needle apparatus 300, and the attachment of the vibration assembly 370 does not interfere with use of the needle apparatus 300 by the operator. As shown in FIG. 6, the removably attachable vibration assembly 370 may include a chamber 372 that may be in two or more sections 372a and 372b. The sections may fit together to contact the handle 326 and have a shape complimentary to the handle 326 to, for example, surround the handle 326 for providing vibration to a post 364 of the handle 326. Alternatively, the chamber 372 may be a single unit and of any shape that can be mounted on the handle 326 without interfering with the operation of the needle apparatus 300. As shown, the section 372a of the chamber 372 includes a vibrational member 374, an inlet port 376 and an outlet port 378. As described above, a compressed air source or other energy source may enter the inlet 376 to cause the vibrational member 374 to vibrate within the chamber 372. Any of the vibration assemblies described herein may be removably attachable to the handle of the needle as can be understood by one of skill in the art.

Figure 7:
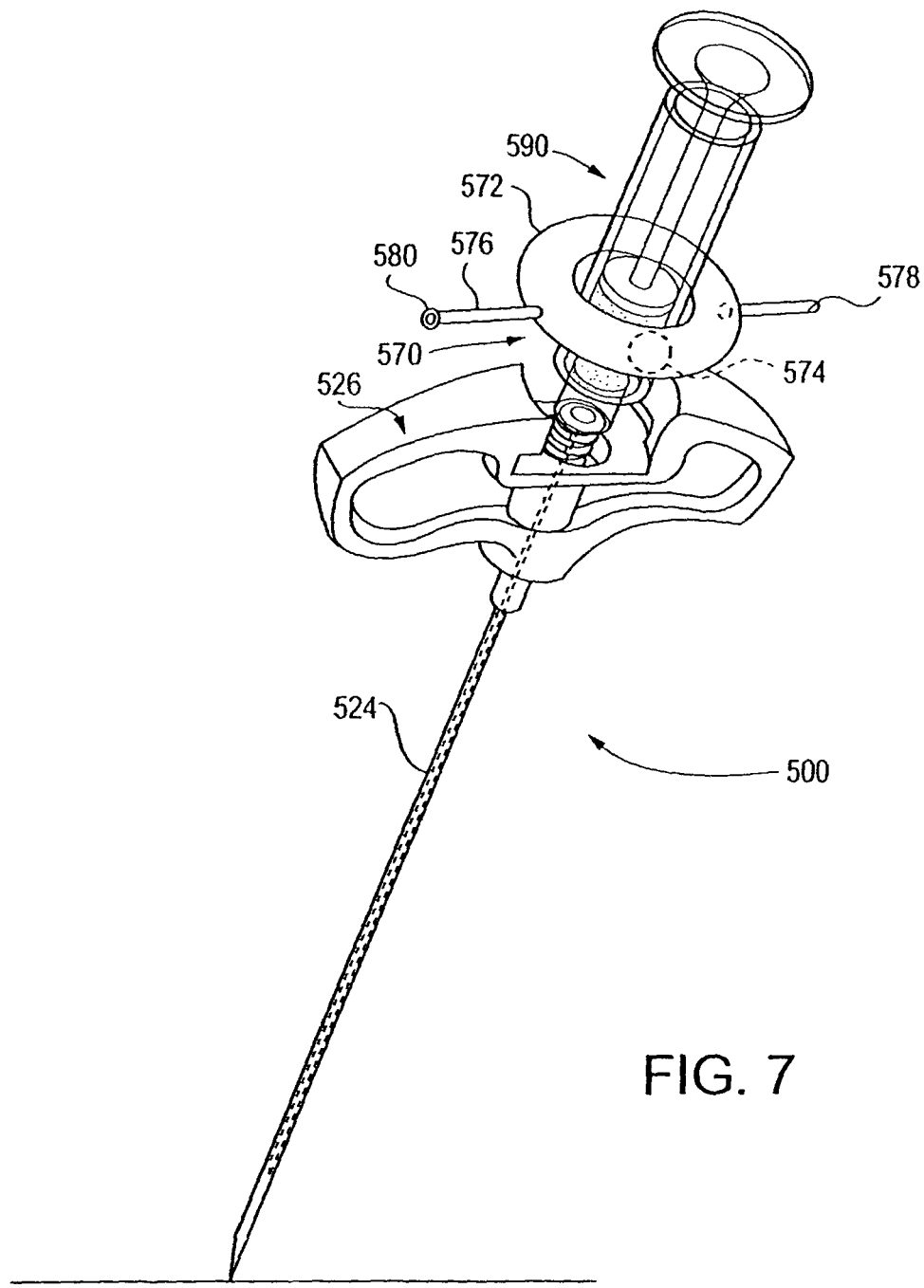
FIG. 7 is a perspective view of another cement delivery needle apparatus.

A further cement delivery needle apparatus 500 is shown in FIG. 7. The needle apparatus 500 is similar to the needle shown in FIGS. 3A and 3B where an injector 590 is connected to a handle 526. As shown in FIG. 7, the needle apparatus 500 includes a vibration assembly 570 disposed against the injector 590 for agitating the cement 36 for injection of the cement 36 into the vertebral body 32 through the sheath 524. The vibration assembly 570 may be constructed as part of the injector 590, for example, but not limited to integrally molding the vibration assembly 570 at least partially into the injector 590. Alternatively, the vibration assembly 570 may be removably connected to the injector 590 once the needle apparatus 500 is inserted into the vertebral body 32. The cement 36 may be agitated prior to injection, during injection or any combinations thereof.

As shown in FIG. 7, the vibration assembly 570 may include a chamber 572 surrounding the injector 590. The chamber 572 may contain vibrational member 574, for example, a dense metallic spherically shaped body, such as a ball bearing. A plurality of vibrational members 574 may be in the chamber 572. The vibrational member(s) 574 and the chamber 572 may be radiolucent. Other vibrational members known to one of skill in the art, such as a roller that may be cylindrical, tapered, or spherically shaped, may be used in the chamber 572. The chamber 572 may further include an inlet port 576 and an outlet port 578. Alternatively, a plurality of outlet ports 578 may exit from the chamber 572, similar to the plurality of ports shown in FIG. 3. The inlet port may include a Luer connector 580 for attachment of tubing 82 connected to a compressed air source or other energy source (not shown). Operation of the vibration assembly is as described above. Alternatively, a vibration assembly similar to the vibration assembly 270 in FIG. 5 may be operatively connected to the injector 590.

Figure 8:
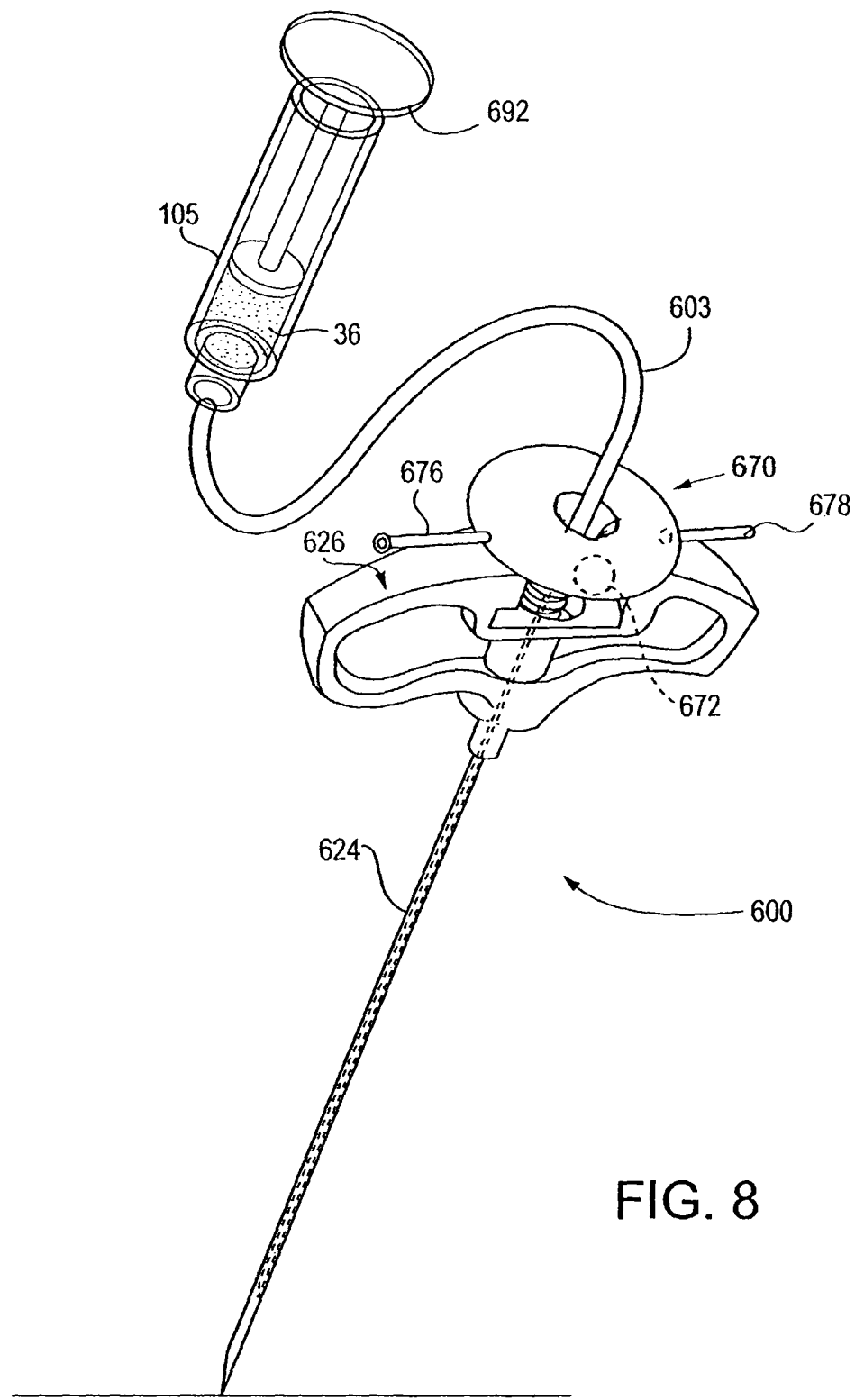
FIG. 8 is a perspective view of another cement delivery needle apparatus.

A cement delivery needle apparatus 600 having a vibration assembly 670 that may be disposed against a connector 603 is shown in FIG. 8. The vibration assembly 670 is similar to the vibration assemblies described above with the exception that the vibration assembly 670 is disposed against the connecting tube 603 instead of the injector 590 as described above and shown in FIG. 7. Operation of the vibration assembly 670 is as described above. Alternatively, a vibration assembly similar to the vibration assembly 270 in FIG. 5 may be operatively connected to the connecting tube 603.

The cement delivery needle apparatus 20, 200, 300, 500, 600 may be 10, 11, 13, or 14 gauge depending on where the needle is to be used. Generally, 10 or 11 gauge needles are used for delivery of cement to a vertebral body in a lumbar or sacral vertebra and 13 or 14 gauge needles are used for delivery of cement to a vertebral body in a thoracic or cervical vertebra. The cement delivery needle apparatus 20, 200, 300, 500, 600 may be about eight cm to about twenty cm in length. For example, the cement delivery needle apparatus 20, 200, 300, 500, 600 may be about ten cm to about fifteen cm in length. Thin walled, large lumen needles, having a similar outer diameter as the needles described above and an increased inner diameter may also be used. The insert 28 described above provides strength for insertion of the thin walled, large lumen needles. However, one of skill in the art will recognize that the size and proportions of the cement delivery needle apparatus 20, 200, 300, 500, 600 may vary depending on the vertebral body being filled and the subject. For example, the cement delivery needle apparatus 20, 200, 300, 500, 600 may be made as radiolucent as possible to assist the operator in positioning the needle apparatus 20, 200, 300, 500, 600 in the vertebral body 32. The needle apparatus 20, 200, 300, 500, 600 may be reusable or disposable.

Figure 10:
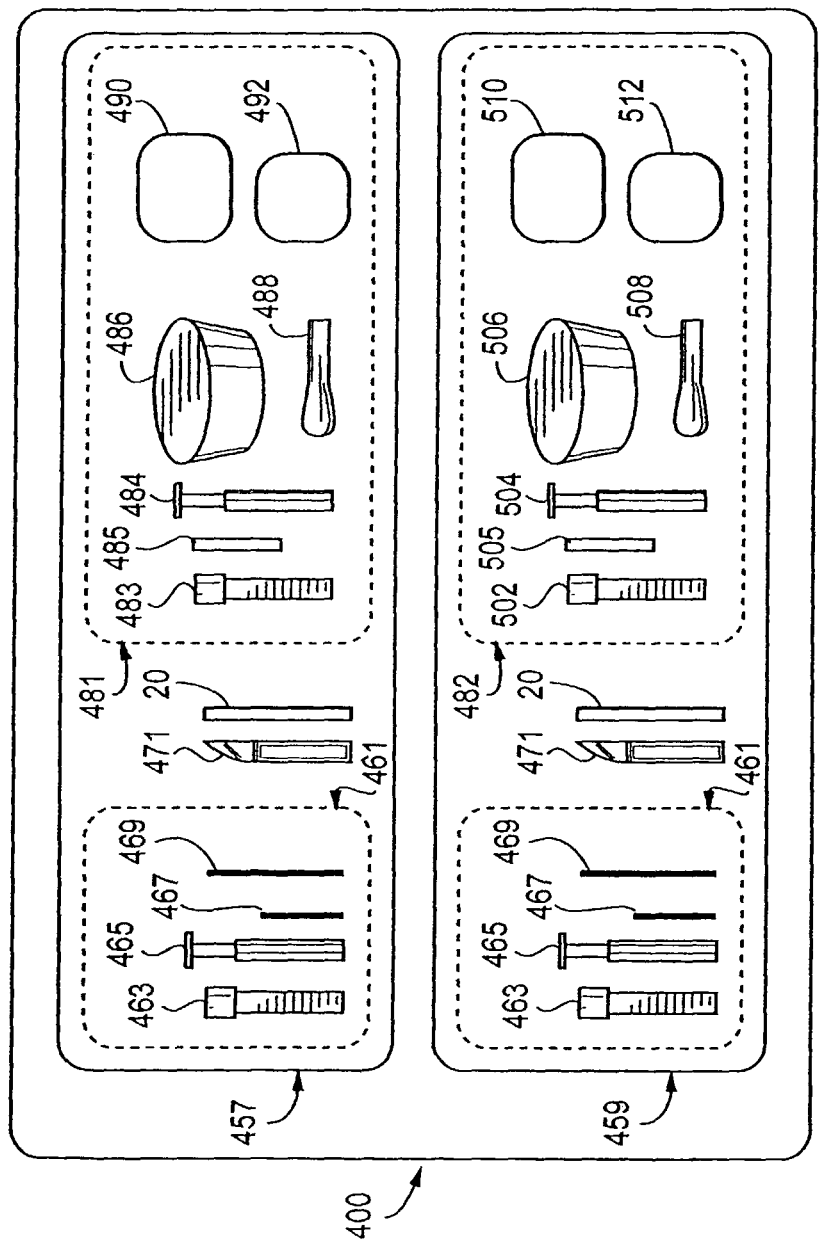
FIG. 10 is a schematic representation of a kit for vertebroplasty.
Figure 11:
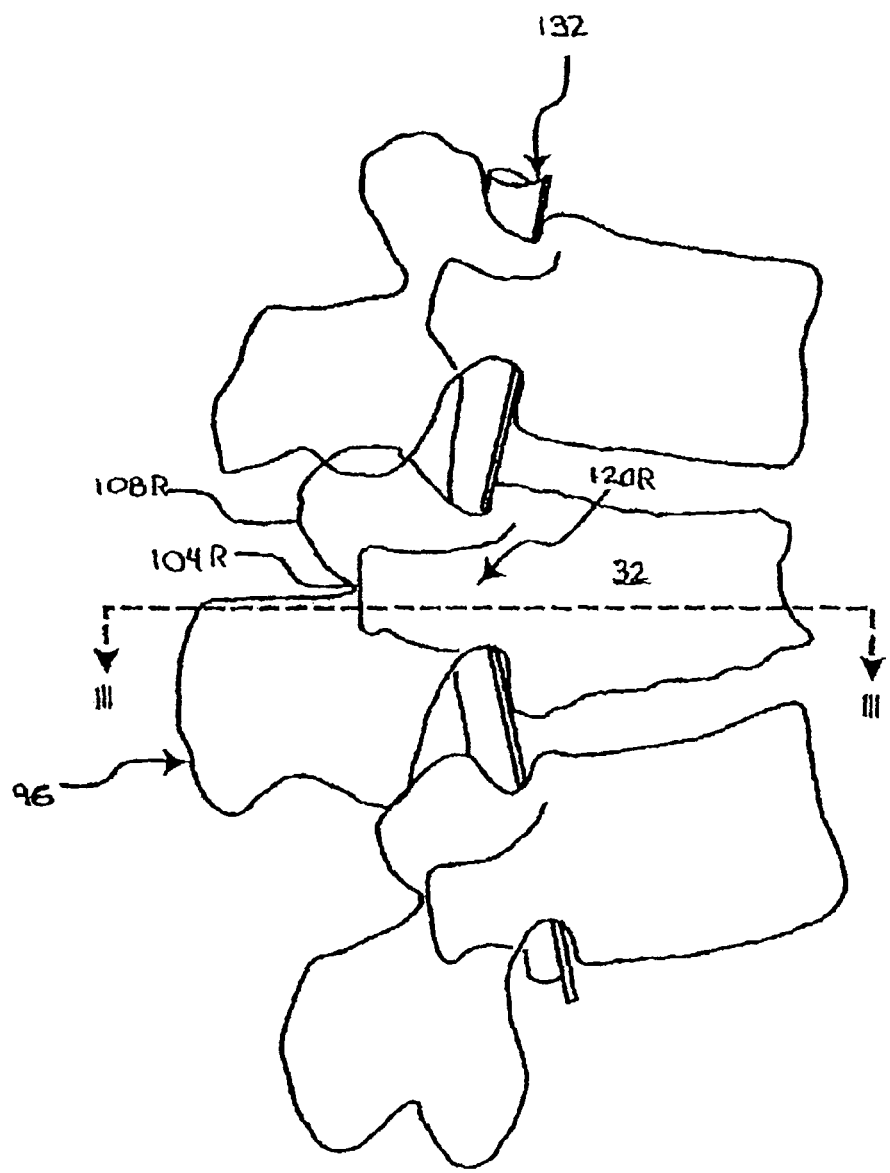
FIG. 11 is a lateral view of 3 vertebrae where the middle vertebra has a condition suitable for treatment by vertebroplasty.

As shown in FIG. 10, the needle apparatus 20, 200, 300, 500, 600 may be part of a kit 400 for performing vertebroplasty. Kit 400 may have a first tray 457 and a second tray 459. Each tray 457, 459 may be housed within sterile packaging for storage until use and may include a local anesthesia assembly 461, a surgical cutting instrument 471 such as a scalpel, a cement delivery needle, such as the needle apparatus 20, 200, 300, 500, 600 described, and a cement mixing assembly 481, 482 respectively, for preparing the cement 36. The anesthesia assembly 461 may include a vial of local anesthesia 463, a syringe 465 for administering the anesthesia, a needle 467 for anesthesia aspiration and a long needle 469 for anesthesia injection.

The cement mixing assemblies 481 and 482 of the trays 457, 459, respectively, may have different components for preparing cement having different imaging properties. The mixing assembly 481 of the tray 457, for example, may include a monomer liquid 483 in a vial, a monomer compatible aspiration syringe 484, a monomer aspiration needle 485, a mixing bowl 486, a mixing spatula 488, a polymer powder 490, and a first opacifier 492. The mixing assembly 482 of the tray 459 may include components similar to the mixing assembly 481 of the tray 457 such as a monomer liquid 502 in a vial, a monomer compatible aspiration syringe 504, a monomer aspiration needle 505, a mixing bowl 506, a mixing spatula 508, a polymer powder 510. The mixing assembly 482 may also include an opacifier 512 that may be of a different density than the first opacifier 492 of the mixing assembly 481. Alternatively, the densities of the opacifiers 492, 512 may be the same. The components of the trays are described in detail in application Ser. No. 09/594,685 which is incorporated by reference in its entirety herein. One of skill in the art will recognize that the trays 457, 459 may contain additional or alternative components for performing vertebroplasty.

Figure 12:
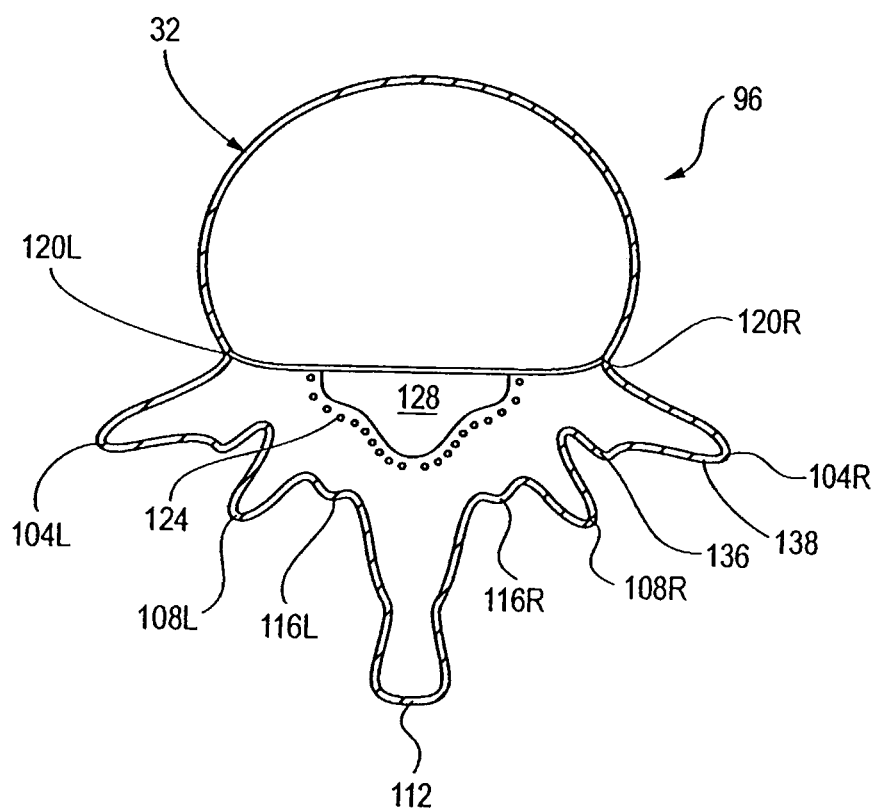
FIG. 12 is an axial view of the compressed vertebra through line III-III of FIG. 9.
Figure 13A:
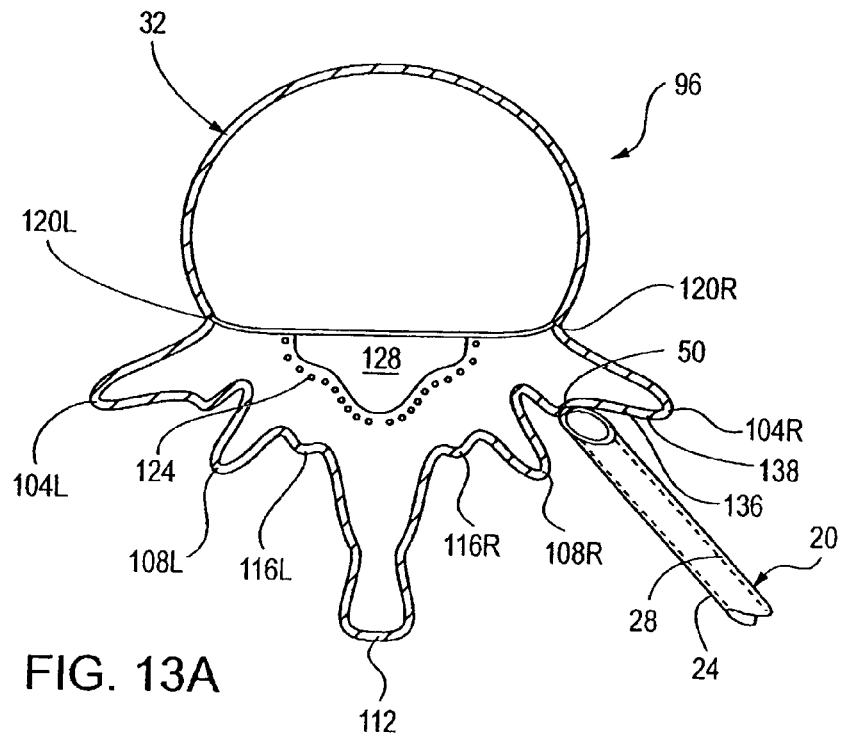
FIG. 13A is an axial view of the vertebra in FIG. 12 showing the insertion of the cement delivery needle apparatus in FIG. 1 in a transpedicular approach.
Figure 13B:
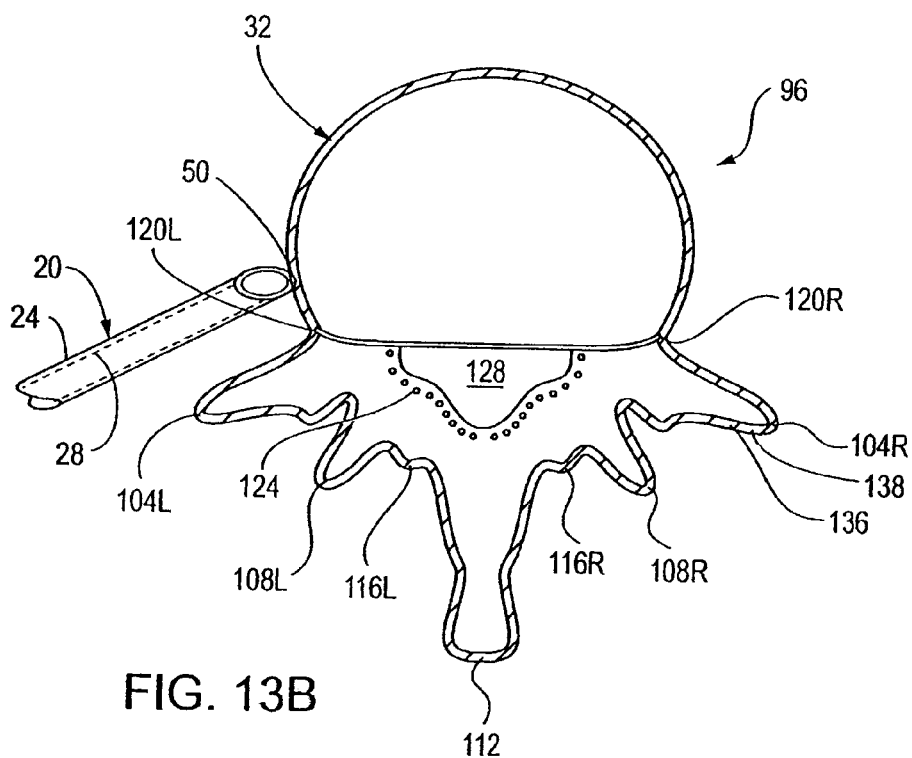
FIG. 13B is an axial view of the vertebra in FIG. 12 showing the insertion of the cement delivery needle apparatus in FIG. 1 in a lateral approach.
Figure 13C:
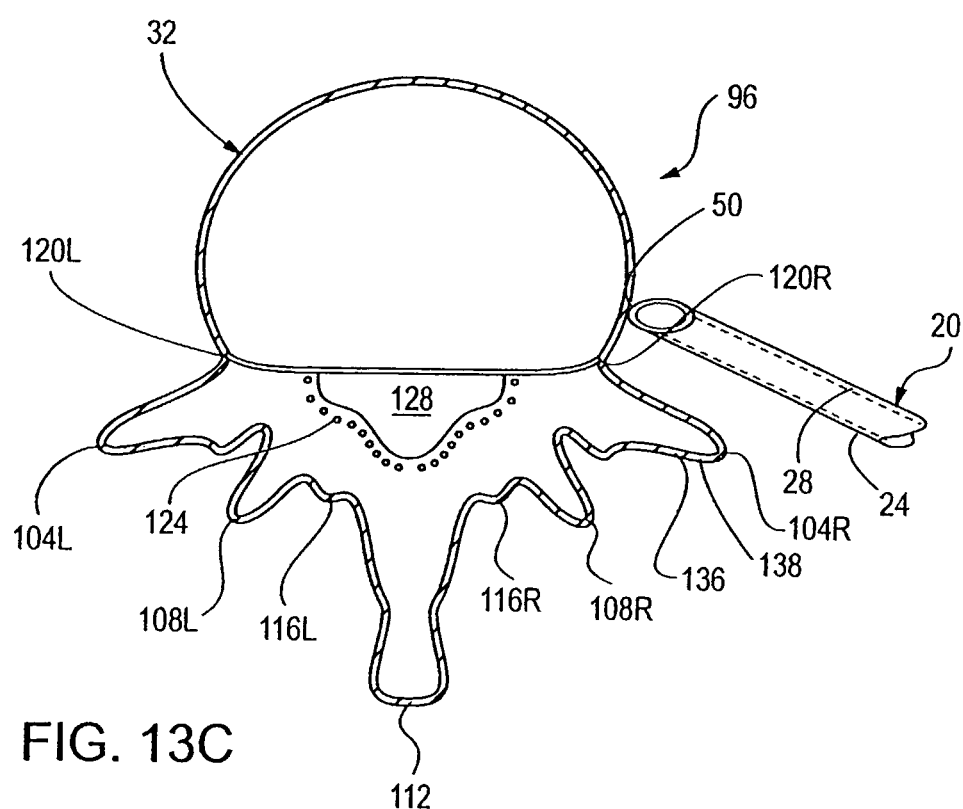
FIG. 13C is an axial view of the vertebra in FIG. 12 showing the insertion of the cement delivery needle apparatus in FIG. 1 in a parapedicular approach.
Figure 14A:
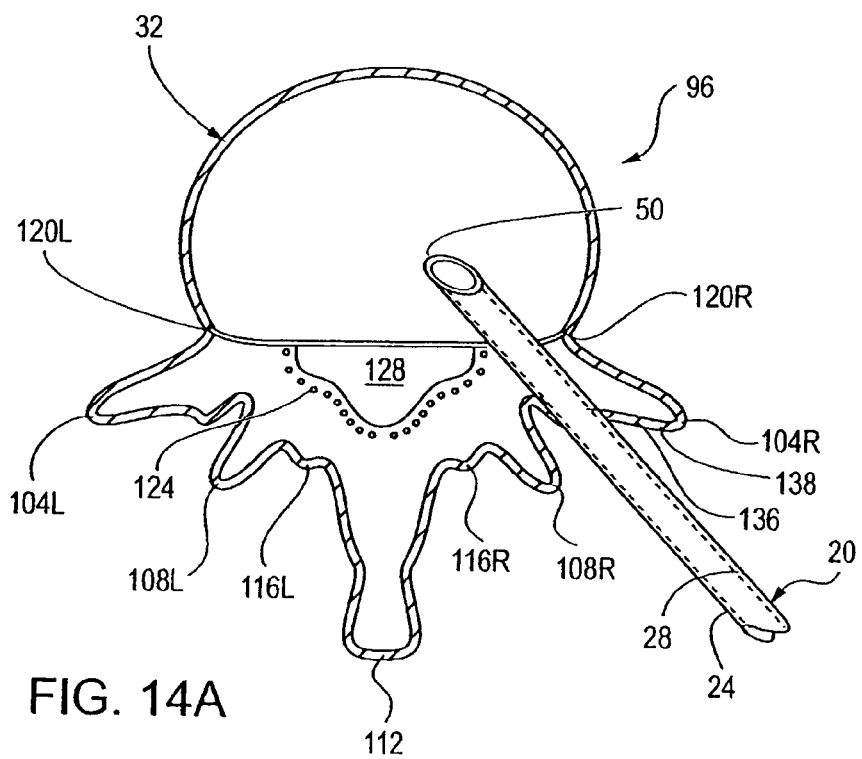
FIG. 14A is an axial view of the vertebra in FIG. 12 showing the insertion of the cement delivery needle apparatus in FIG. 1 to the transition from the right pedicle to the vertebral body.
Figure 14B:
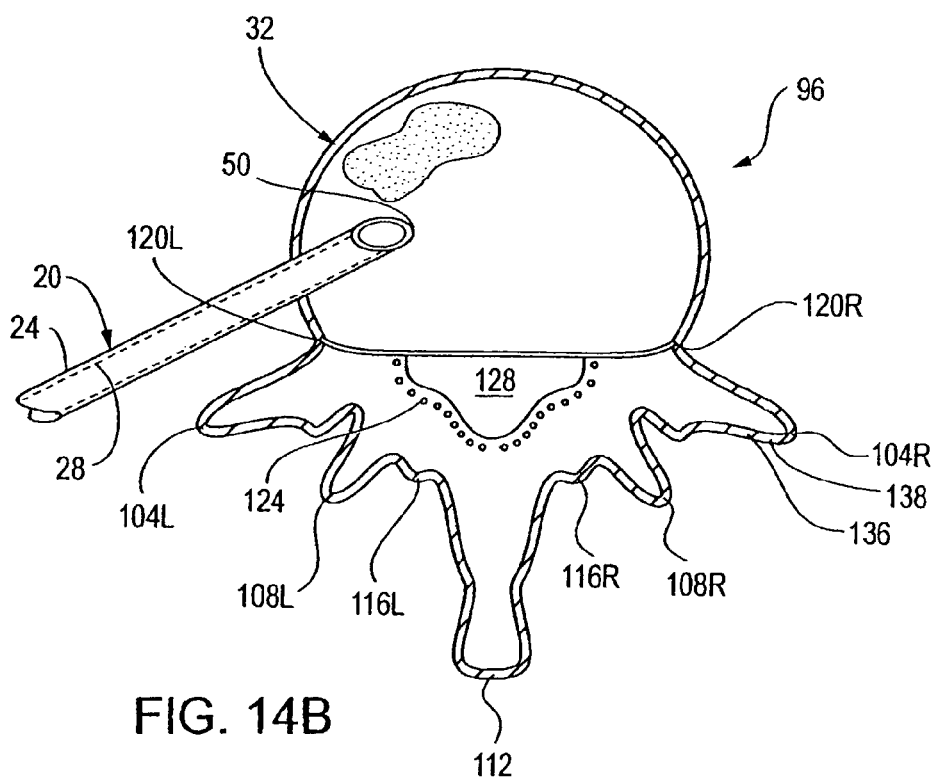
FIG. 14B is an axial view of the vertebra in FIG. 12 showing the insertion of the cement delivery needle apparatus in FIG. 1 inserted into the vertebral body.

The use of the needle apparatus 20 to perform vertebroplasty on the vertebra 96 is shown in FIGS. 11-15 As shown in FIG. 12, vertebra 96 has a right and left transverse process 104R, 104L, a right and left superior articular process 108R, 108L, and a spinous process 112 at the posterior of vertebra 96. Right and left lamina 116R, 116L lie intermediate to the spinous process 112 and the superior articular processes 108R, 108L, respectively. Right and left pedicles 120R, 120L and lamina 116R, 116L cooperate to form a vertebral arch 124. The vertebral body 32 is located at the anterior of the vertebra 96, and is joined to the arch 124 at the pedicles 120R, 120L. The arch 124 and the vertebral body 32 define the spinal canal 128 through which the spinal cord 132 passes. A periosteum 136, a layer of tissue, covers a cortex 138. The cortex 138 is the outer surface of the vertebra 96.

The patient is placed in the prone position so that the vertebra 96 is within the field of an imaging device such as an X-ray projection fluoroscopy imaging device. Other imaging devices can be used, as will occur to those of skill in the art. When the imaging device is "on", the vertebra 96 is projected onto a display. The skin overlying the vertebra 96 is prepped and draped in the usual manner with sterile technique, as will be understood by those of skill in the art. Instruments and supplies required for the vertebroplasty procedure may be supplied in the kit 400. An anesthetic is injected into the skin, underlying fat and into the periosteum 136 of the pedicle to be entered. For explanatory purposes it is assumed that the right pedicle 120R will be entered first. Next, a skin incision of about five millimeters is made using a scalpel, such as the scalpel 71 in the kit 400.

At this point, the needle apparatus 20 is grasped by the operator. Typically, the needle 20 is grasped by the operator such that the palm of the operator's hand abuts the complementary connector 84 and the operator's fingers are folded around wings 56 of handle 26. Thus, the sheath 24 with the insert 28 received therein, protrudes between the fingers of the operator.

Figure 15:
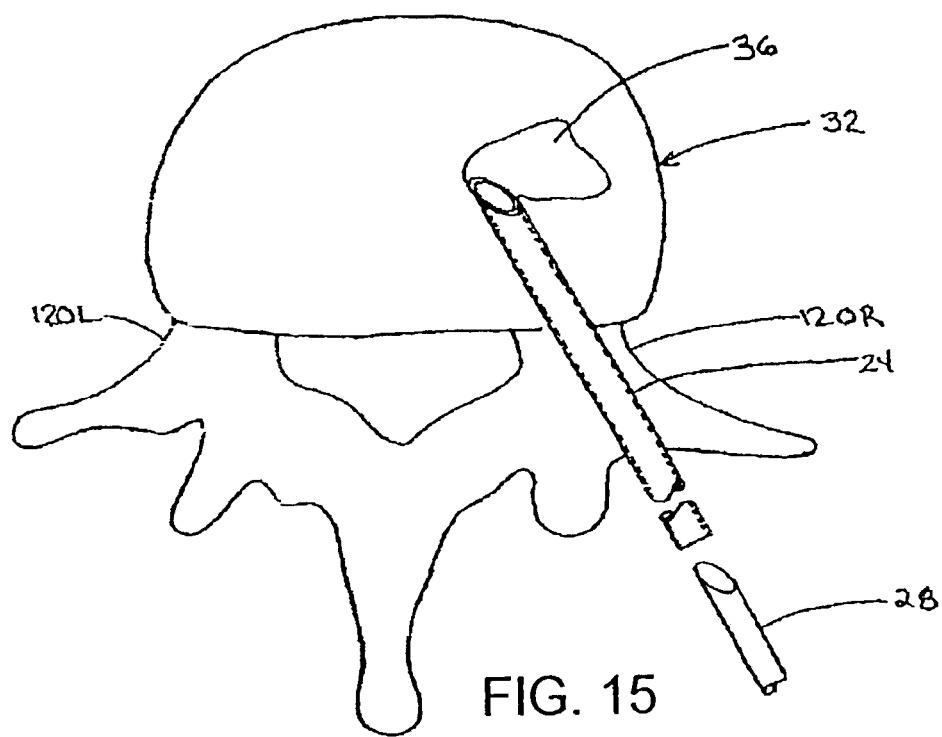
FIG. 15 is an axial view of the vertebra in FIG. 12 showing the insertion of the cement delivery needle apparatus in FIG. 1 inserted into the vertebral body where the insert is removed from the sheath and cement is delivered to the vertebral body.

As shown in FIGS. 13-16, the needle apparatus 20 is inserted into the incision and passed down the right pedicle 120R, for example, until it enters the vertebral body 32 and reaches the junction of the anterior and middle thirds. The needle apparatus 20 is inserted until the tip 50 meets the periosteum 136, as shown in FIG. 13A. As shown in FIGS. 13B and 13C, lateral and parapedicular approaches are also possible for insertion of the needle apparatus 20 into the vertebral body 32. Additional applied force is then required to pass through the periosteum 136 and the cortex 138 and into the right pedicle 120R. The needle apparatus 20 with the tip 50 is inserted further to the transition from the right pedicle 120R to the vertebral body 32, as shown in FIG. 14A illustrating the transpedicular approach. Again, additional applied force is required to pass through the transition and into the vertebral body 32. The needle apparatus 20 is further inserted until the tip 50 reaches the junction of the anterior and middle thirds of the vertebral body 32, as shown in FIG. 14A. FIG. 14B illustrates needle apparatus 20 insertion for lateral and parapedicular approaches. At this point the complementary connector 84 may be released from the connector 60 and the insert 28 is slidably removed from the sheath 24. The position of the sheath 24 is maintained such that the tip 50 is still in the vertebral body 32 after the insert 28 is removed from the sheath 24 as shown in FIG. 15.

The cement 36 for strengthening the vertebral body 32 may then be prepared. The prepared cement 36 is inserted into the syringe 92 and the syringe 92 is releasably connected to the connector 60 of the handle 26. Alternatively, the syringe 92 is releasably attached to the connecting tubing 105 which is releasably attached to the connector 60.

The vibration assembly 70 on the handle 26 may be activated prior to the injection of the cement 36 through sheath 24 and into vertebral body 32. The vibration assembly 70, as shown in FIG. 1, may be activated by supplying a source of compressed air to the inlet 76 that enters the chamber 72 to activate the vibrational member 74. The flow of air continues out through the outlet 78. The vibrational member 74 may oscillate within the chamber 72 causing vibration of the post 64 and the cement 36 flowing therethrough. The frequency of the oscillations may be such that the flow of the cement transitions from laminar flow to particulate ball bearing flow where the particles move more easily than the laminar flow. The frequency of the oscillation will vary with the chemical properties of the cement 36, for example, the particular cement preparation, the amount of radiodense material added and the particle size The vibration assembly 70 may be operational prior to or during injection of the cement 36 or both. The vibration assembly 70 improves the flow of the cement 36 to particulate, ball bearing flow and thus, reduces the amount of pressure required to inject the cement 36 from the syringe 92 through the hollow interior 68 of the handle 26 and through the sheath 24 into the vertebral body 32. Without vibration of the cement, the intravertebral pressure exerted during injection may range from about 150 mm Hg (2.9 psi) with a hand crank injector to about 500 mm Hg (9.7 psi) with a plunger type applicator. The injector device itself may be capable of generating pressure by hand of between 800 and 1400 psi. The pressure applied to the plunger 94 of the syringe 92 to express the cement 36 when using the vibration assembly 70 to agitate the cement 36 may be less than about 800 psi, for example less than about 700 psi. The decreased injection pressure may help avoid undesirable extrusion of the cement into the veins that may continue even after the pressure on the injector is removed when the cement is injected with an injector exerting greater than 1200 psi.

The direction of the cement 36 injected into the vertebral body 32 may be controlled as the cement 36 is ejected from the beveled outlet 40. Thus, the sheath 24 may be turned to aim the beveled outlet 40 and thereby direct the flow of the cement 36 in the vertebral body 32. As filling of the vertebral body 32 progresses, the sheath 24 may be rotated about the axis 46 to direct the cement 36 in a preferred direction or to direct the cement 36 away from a disc space of the vertebra 96, as desired. Delivery of the cement 36 may be observed by an imaging device, including, for example, x-ray, ultrasonic, magnetic resonance or other visual guidance devices.

At this point, a decision may be made as to whether a sufficient quantity of the cement 36 has been injected. This decision is made using known criteria and is typically made by the radiologist, physician or other vertebroplasty professional who is performing the method. If it is determined that enough of the cement 36 has been injected to provide the desired strength to the vertebral body 32, pressure by the user on the plunger is removed and the vibration assembly 70 may be turned off by stopping the flow of compressed air and the flow of the cement 36 stops. When the vibration of the vibration assembly 70 is stopped, the flow of the cement 36 returns to laminar flow thus requiring greater pressure, i.e., greater than 800 psi, if the cement 36 is continued to be expressed. Once the desired amount of the cement 36 has been delivered to the vertebral body 32, the treatment method is complete. If it is determined that not enough of the cement 36 has been injected into the vertebral body 32, then a second injection may be performed by inserting the needle apparatus 20 through the other pedicle, in this case the left pedicle 120L. For the second injection, the second density of the cement 36 may be used from the mixing assembly 482 of the kit 400.

The use of the needle apparatus 200 shown in FIG. 5 may be similar to the use of the needle apparatus 20 described above with the exception of the operation of the vibration assembly 270. As described above for the vibration assembly 70, the vibration assembly 270 on the handle 226 may be activated prior to the injection of the cement 36, during injection or both. Activation of the vibration assembly 270 may cause the flow of the cement 36 to transition from laminar flow to particulate, ball bearing flow. The vibration assembly 270 may be activated by the switch 286. The vibrational speed of the assembly 270 may also be controlled by the switch 286. When the switch 286 is "on", power may be supplied to the motor 276 from the driver assembly 278 to move the arm 274. The arm 274 may provide vibration to the post 264 of the handle 226. Once the desired amount of the cement 36 has been delivered to the vertebral body 32, the switch 286 may be turned "off" and the pressure on the plunger removed to stop the flow of the cement 36.

The use of the needle apparatus 300 shown in FIG. 6 may be similar to the use of the needle apparatus 20 described above with the exception of the attachment of the vibration assembly 370 to the handle 326. The needle apparatus 300 may be inserted into the vertebral body as described above without having the vibration assembly 370 attached to the handle 326. This may assist the operator in clearly viewing the vertebral body 32 for insertion and operation of the needle apparatus 300 until the needle has been positioned in the vertebral body 32. The complementary connector 384 and the insert 328 may then be slidably removed from the sheath 324. The vibrational assembly 370 may then be attached to the handle 326 while the sheath 324 remains in position in the vertebral body 32. Operation of the vibration assembly 370 once the assembly is attached to the handle 326 may be as described above for the vibration assembly 70.

This application is not limited to the particular examples described above. The individual components of the described system may be combined in any suitable manner to practice the system according to the respective demands of the user. In addition, while various aspects of the invention have been described, it will be apparent to those of ordinary skill in the art that many more aspects and implementations are possible within the scope of the invention. Accordingly, the invention is not to be restricted except in light of the attached claims and their equivalents.

The invention claimed is:

1. A bone cement delivery needle apparatus comprising:
a needle comprising a sheath; said sheath having an inlet to receive a bone cement and an outlet, said outlet being configured and operative to penetrate a vertebral body, for expressing the cement into said vertebral body;
a handle connected to the sheath for applying bone-penetrating force to the sheath;
a passageway through the handle, the passageway having a first end at one side of the handle for receiving the bone cement and a second end at another side of the handle for passing the bone cement to said inlet of said sheath;
said sheath extending in series from said second end of said passageway; and
a vibration assembly comprising a toroidal chamber coupled to the handle and surrounding the passageway at a position between said first and second ends of said passageway, an inner perimeter of the chamber engaging an outer wall of the passageway; the chamber containing a vibrational member that oscillates in the chamber in response to energy supplied to the chamber for agitating the bone cement as the bone cement traverses the passageway.

2. The needle apparatus of claim 1 further comprising a removable insert within at least a portion of the sheath.

3. The needle apparatus of claim 1 where the vibration assembly comprises an energy source operably connected to the vibration assembly.

4. The needle apparatus of claim 1 where the vibrational member is adapted for rolling within the chamber.

5. The needle apparatus according to claim 1, wherein said passageway comprises an injector removably connected to the handle for delivery of the bone cement to the sheath.

6. The needle apparatus according to claim 1 where the vibration assembly is removably connected to the handle.

7. The needle apparatus according to claim 1 where the vibration assembly is at least partially integrally formed with the handle.

8. The needle apparatus according to claim 1 where the vibration assembly comprises an arm for providing vibration to the handle.

9. The needle apparatus of claim 8 further comprising a motor for driving the arm.

10. The needle apparatus according to claim 1 where at least a portion of the needle apparatus is disposable.

11. The needle apparatus according to claim 1 where at least a portion of the needle apparatus is at least partially radiolucent.

12. A method for delivering fluid bone cement to a target site comprising the steps of:
providing a fluid bone cement delivery needle apparatus having:
a needle comprising a sheath; said sheath having an inlet to receive a bone cement and an outlet, said outlet being configured and operative to penetrate a vertebral body, for expressing the cement into said vertebral body;
a handle connected to the sheath for applying bone-penetrating force to the sheath;
a passageway through the handle, the passageway having a first end at one side of the handle for receiving the bone cement and a second end at another side of the handle for passing the bone cement to said inlet of said sheath;
said sheath extending in series from said second end of said passageway; and
a vibration assembly comprising a toroidal chamber coupled to the handle and surrounding the passageway at a position between said first and second ends of said passageway, an inner perimeter of the chamber engaging an outer wall of the passageway; the chamber containing a vibrational member that oscillates in the chamber in response to energy supplied to the chamber for agitating the bone cement as the bone cement traverses the passageway; and
agitating the fluid bone cement with the vibration assembly for delivery to the target site.

13. The needle apparatus according to claim 12 where the bone cement comprises polymethyl methacrylate.

14. The method according to claim 12 where the vibration assembly is removably attachable to the handle.

15. The method according to claim 12 further comprising the step of providing an energy source to the vibration assembly.

16. The method according to claim 12 further comprising:
providing an injector removably connected to the needle assembly, the injector being configured and operative for injecting the bone cement; and
applying pressure to the bone cement with the injector.

17. The method of claim 16 where the pressure is less than 800 psi.

18. The method of claim 16 where the pressure is less than 700 psi.

19. The needle apparatus of claim 1, wherein said vibration assembly is disposed within said handle.

20. The needle apparatus of claim 1, wherein said passageway comprises a connector.

21. The needle apparatus of claim 1, wherein said passageway comprises an injector having a barrel for containing said bone cement.

22. The needle apparatus of claim 1, wherein said vibration assembly is disposed within said handle.

23. The needle apparatus of claim 1, wherein said passageway comprises a connector.

24. The needle apparatus of claim 1, wherein said passageway comprises an injector having a barrel for containing said bone cement.

25. The method of claim 12, wherein said vibration assembly is disposed within said handle.

26. The method of claim 12, wherein said passageway comprises a connector.

27. The method of claim 12, wherein said passageway comprises an injector having a barrel for containing said bone cement.

28. The needle apparatus of claim 1, wherein said vibration assembly is separable from said passageway.

29. The needle apparatus of claim 28, wherein said vibration chamber is formed by a plurality of separable chamber segments.

30. The needle apparatus of claim 1, wherein said vibration assembly is separable from said passageway.

31. The needle apparatus of claim 1, wherein said vibration chamber is formed by a plurality of separable chamber segments.

* * * * *